Oct. 19, 1965 C. FISCHER Plant Pat. 2,561
GLADIOLUS PLANT
Filed April 15, 1964
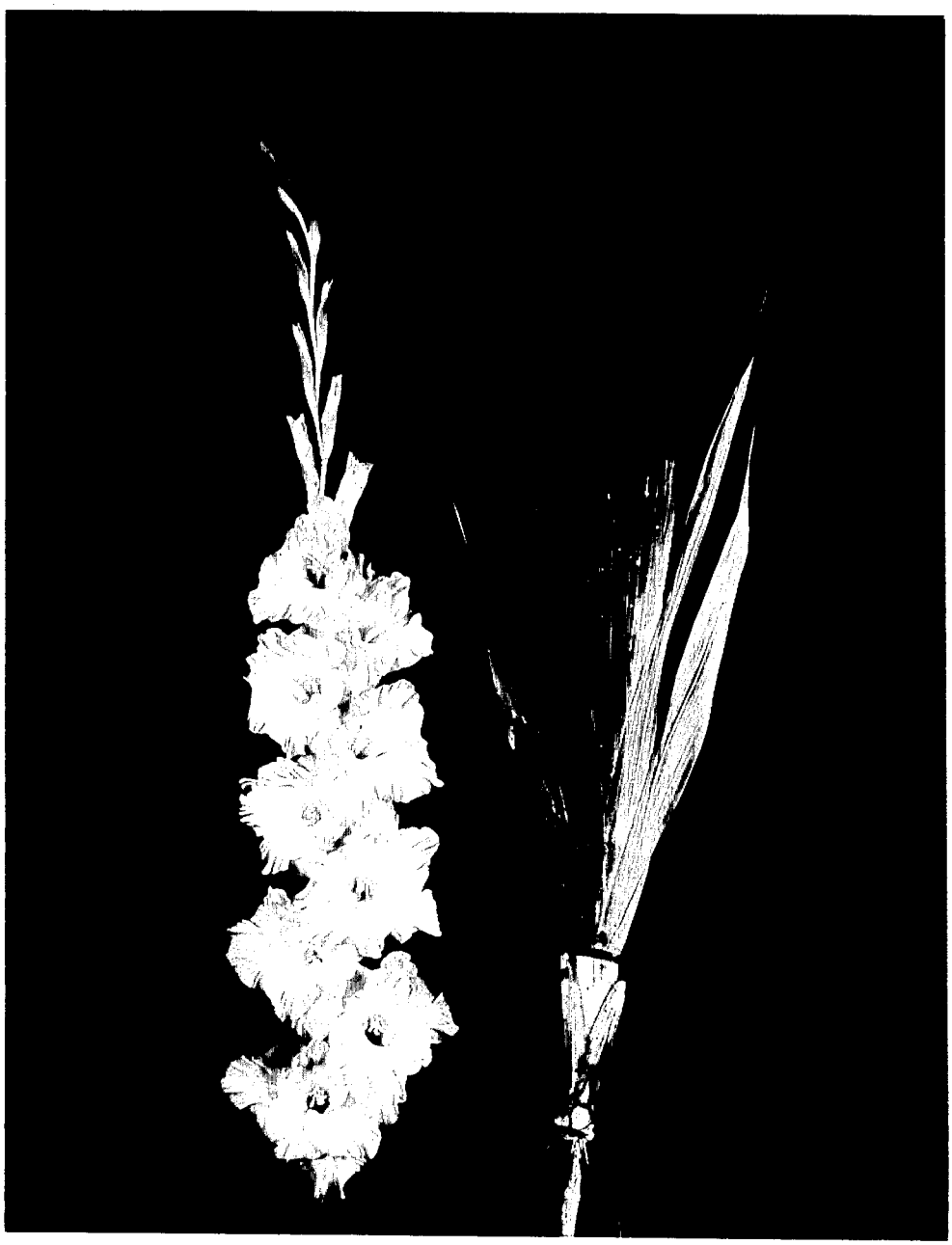
Inventor.
Carl Fischer
By: Robb & Robb
Attorneys.

United States Patent Office

Plant Pat. 2,561
Patented Oct. 19, 1965

2,561
GLADIOLUS PLANT

Carl Fischer, St. Charles, Minn., assignor to Imperial Flowers Limited, Leamington, Ontario, Canada, a corporation of Canada Filed Apr. 15, 1964, Ser. No. 360,154
1 Claim. (Plt.—85)

The present invention relates to a new and distinct variety of gladiolus plant which was orignated by me by crossing unnamed and unpatented mixed seedlings used as both seed and pollen parents.

As the result of this breeding, I have produced a new and improved gladiolus variety, as evidenced by the following unique combination of characteristics which are outstanding therein and which distinguish it from its parents, as well as from all other varieties of which I am aware:

(1) An ability to propagate rapidly;
(2) Upright foliage;
(3) Excellent flower opening qualities;
(4) A ruffled flower form; and
(5) A distinctive, attractive, clear and smooth orange flower color.

My new variety resembles the variety known as "Fire Opal" (unpatented) more than any other variety, but differs principally therefrom by a much taller habit of growth; a longer flowerhead; more heavily ruffled flower; a very different flower color which is a clear, smooth orange color; and it is a much better grower form bulblets.

Asexual reproduction of my new variety by cormels through several generations, as performed by me at St. Charles, Minnesota, and at Oceanside, California, shows that the foregoing characteristics and distinctions come true to form and are established and transmitted through succeeding propagations.

The accompanying drawing shows a typical specimen flower spike and typical foliage of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota, and Oceanside, California.

Propagation: Holds its distinguishing characteristics through succeeding propagations from cormels.

*Plant*

Growth: Excellent propagator; exceptionally good grower from bulblets.

Blooming habit: Blooms in 75 days or less from large bulbs.

Stems: Long and willowy.
*Diameter at base.*—About ⅜ inch.
*Color (at base).*—Deep rose.

Foliage: Upright; arranged in fan-shaped relation on the plant; individual leaves range from 1½ inches to 1¾ inches wide and attain a height of about 36 inches. Color—medium green.

Disease resistance: Average resistance to the usual diseases to which gladiolus varieties are normally subject, as determined by comparison with other varieties grown in Minnesota and in California.

Corms (bulbs): Round; smooth; top of husks have a rose tint. Color of flesh—ivory.

*Flower*

Spike: Blossom spike averages 60 inches tall, with flowerhead ranging from 24 inches to 27 inches long; bears from 18 to 20 buds, with 6 to 8 buds open at one time.

Bud:
*Size.*—About 2¾ inches long when opening.
*Opening.*—Opens well; 5 or 6 buds show color at one time.

Flower:
*Arrangement.*—Florets are semi-formally arranged on stem.
*Size.*—Individual florets average from 5 inches to 5½ inches in diameter.
*Form.*—Florets are ruffled and slightly triangular.
*Keeping qualities.*—Keeps well.

Petals:
*Shape.*—Round; extremely ruffled; needle pointed; somewhat recurved.
*Size.*—Upper petals—about 3 inches wide. Lip petal—about 2 inches wide.
*Aspect.*—Heavy substance; creased surface.
*Fragrance.*—None.
*Color.*—Saturn Red, Plate 13/2, with reverse of florets Saturn Red, Plate 13/1; front shades to a lighter color in the throat; blotch, midribs and veining on reverse are Aureolin, Plate 3/2; has a fine red hairline in the calyx where the petals separate, but not on the lip petals.

*Reproductive organs*

Stamens: Color—cream, with blue on pollen side.
Pistil: Color—cream.

I claim:

A new and distinct variety of gladiolus plant, substantially as herein shown and described, characterized particularly as to novelty by the unique combination of an ability to propagate rapidly, upright foliage, excellent flower opening qualities, a ruffled flower form, and a distinctive, attractive, clear and smooth orange flower color.

No references cited.

ABRAHAM G. STONE, *Primary Examiner.*